US005468254A

United States Patent [19]
Hahn et al.

[11] Patent Number: 5,468,254
[45] Date of Patent: Nov. 21, 1995

[54] METHOD AND APPARATUS FOR DEFIBRILLATION USING A MULTIPHASIC TRUNCATED EXPONENTIAL WAVEFORM

[75] Inventors: Stephen J. Hahn, Roseville, Minn.; David K. Swanson, Mountain View, Calif.

[73] Assignee: Cardiac Pacemakers, Inc., St. Paul, Minn.

[21] Appl. No.: 97,463

[22] Filed: Jul. 26, 1993

[51] Int. Cl.$^6$ ........................................... A61N 1/39
[52] U.S. Cl. ................................................ 607/5
[58] Field of Search ................................. 607/5–8

[56] References Cited

U.S. PATENT DOCUMENTS

| | | | |
|---|---|---|---|
| 4,821,723 | 4/1989 | Baker, Jr. et al. | 128/419 D |
| 4,850,357 | 7/1989 | Bach, Jr. | 128/419 D |
| 4,953,551 | 9/1990 | Mehra et al. | 128/419 D |
| 4,998,531 | 3/1991 | Bocchi et al. | 128/419 D |
| 5,083,562 | 1/1992 | de Coriolis et al. | 128/419 D |
| 5,275,157 | 1/1994 | Morgan et al. | 607/6 |
| 5,352,239 | 10/1994 | Pless | 607/5 |

OTHER PUBLICATIONS

Dixon et al., *Improved Defibrillation Thresholds With Large Contoured Epicardial Electrodes and Biphasic Wave Forms*, Circulation 76, No. 5, 1987, pp. 1176–1184.

Chapman et al., *Comparative Efficacy of Monophasic and Biphasic Truncated Exponential Shocks for Nonthoracotomy Internal Defibrillation in Dogs*, Journal of the American College of Cardiology, vol. 12, No. 3, 1988, pp. 739–745.

Jones, et al., *Decreased Defibrillator–Induced Dysfunction With Biphasic Rectangular Waveforms*, Am. J. Physiol, 247, 1984, pp. H792–H796.

Schuder, et al., *Optimal Biphasic Waveform Morphology for Canine Defibrillation With a Transvenous Catheter and Subcutaneous Patch System*, Abstracts of the 61st Scientific Session, 1988, p. II–219.

Primary Examiner—William E. Kamm
Assistant Examiner—Marianne Parker
Attorney, Agent, or Firm—Peter Forrest

[57] ABSTRACT

A method and apparatus for converting an arrhythmia of a heart using a biphasic truncated exponential waveform wherein the first phase is of shorter duration than the second phase.

16 Claims, 3 Drawing Sheets

METHOD AND APPARATUS FOR DEFIBRILLATION USING A MULTIPHASIC TRUNCATED EXPONENTIAL WAVEFORM

BACKGROUND OF THE INVENTION

1. Field of the Invention

The present invention relates, generally, to the field of defibrillators. More particularly, it relates to an improvement in the efficacy of cardioverter-defibrillators (ICD). Automatic implantable cardioverter-defibrillators (AICDs) or ICDs customarily include a sensor and sensing circuit to determine when a therapeutic shock is needed, a control circuit to determine what type of therapeutic shock is appropriate, a long-term energy source, such as a battery, a short-term energy storage means such as high-voltage capacitor, and a circuit for transferring electrical energy first from the battery to the capacitor and then from the capacitor to the heart by discharging the capacitor in waveforms having particular shapes, durations, and sequences, to electrodes which deliver the energy as a shock to a heart which is to be converted.

Development of implantable cardioverter-defibrillators since their introduction in the mid 1980s, has not only been directed toward improving their reliability in terms of delivering defibrillation pulses when fibrillation of the heart is detected, but also toward increasing their efficacy. That is, to apply to a heart the minimum amount of energy necessary to ensure conversion. By decreasing the amount of energy required for conversion or defibrillation, the physical size of the implanted automatic defibrillator can be decreased by reducing the physical size of the battery, the capacitor, and other components. A decrease in energy requirements also means that even if the defibrillator is with some degree of frequency called upon to defibrillate a heart, the battery will have a longer life. Thus, extending the period of time before which the defibrillator must be replaced.

Advances in reducing the energy required for defibrillation have been made in the past in various ways. The electrodes delivering the defibrillation shocks to the heart have been improved. It has also been found that shocks of particular shapes, durations, and polarities are more effective in defibrillating the heart. This invention relates to further improvements in the shape of the shocks.

2. Description of Related Art Including Information Disclosed Under Secs. 1.97-1.99

In a paper entitled: *DECREASED DEFIBRILLATOR-INDUCED DYSFUNCTION WITH BIPHASIC RECTANGULAR WAVEFORMS;* by Janice L. Jones and Ronald E. Jones, AM. J. Physiol. 247 (Heart Circ. Physiol. 16); H792–H796, 1984, a study is reported on the characteristics of the negative second portion of a biphasic waveform which best ameliorates postshock dysfunction. The study was based on the use of chick embryo cultured myocardial cells. The article concluded that "the negative tail can only partially reverse the deleterious effects of the leading portion of the waveform and that this effect can be produced either by a low amplitude undershoot that lasts for a long time or by a higher amplitude undershoot that lasts for a shorter time." While this work did find that some waveshapes with the second phase longer than the first reduced dysfunction, dysfunction has never been shown to have a impact on defibrillation efficacy.

The paper *Improved Defibrillation Thresholds with Large Contoured Epicardial Electrodes and Biphasic Waveforms;* by Ellen G. Dixon, circulation 76, No 5 1176–1184, 1987, is primarily concerned with the testing of large contoured patch electrodes on dogs. The electrodes were tested with monophasic, biphasic, and triphasic waveforms. Further, the biphasic waveforms were tested with the first phase being both longer than and shorter than the second phase. It is reported that biphasic waveforms, with the durations of the first and second phases equal, have a significantly lower threshold voltage than a monophasic waveform.

Furthermore, the defibrillation threshold voltage and energy were reported to be significantly higher for biphasic waveforms in which the relationship of the duration of the first to the second phase were 25/75 and 35/65, compared to 50/50, even though the initial voltage of the first phase was of a greater magnitude than the second, with the trailing voltage of the first phase being equal to the beginning voltage of the second phase.

Thus, while this paper was primarily directed to research with respect to electrodes, it does present data indicating that the duration of the first phase of a biphasic waveform should be equal to or longer than that of the second phase. This conclusion was based upon an earlier postulation by Jones et al that the first phase conditions the heart cells to allow more effective defibrillation by the second phase.

The paper, *Comparative Efficacy of Monophasic and Biphasic Truncated Exponential Shocks for Nonthoracotomy Internal Defibrillation in Dogs;* by Peter D. Chapman, et al, Journal of the American College of Cardiology, Vol. 12, No. 3, September 1988 pages 739–745, reports the efficacies of monophasic and biphasic truncated exponential shocks in dogs. The monophasic shocks were compared with biphasic shocks having relative $P_1$ (first phase) versus $P_2$ (second phase) durations of (50 and 50%, 75 and 25%, 90 and 10%, 25 and 75%, 10 and 90%) It was concluded that biphasic shocks with $P_1$ (initial positive phase) longer than $P_2$ (terminal negative phase) markedly reduced energy requirements for nonthoracotomy canine defibrillation and may, therefore, facilitate development of nonthoracotomy devices for clinical applications. The paper further reports that biphasic pulses with the second phase longer than the first phase (25 and 75% and 10 and 90% configurations) resulted in energy thresholds that were significantly higher than even those for monophasic shocks.

The paper: *Optimal Biphasic Waveform Morphology for Canine Cardiac Defibrillation with a Transvenous Catheter and Subcutaneous Patch System,* by John C. Schuder, et al, Circulation, vol 78, II–219, 1988 set forth that previous studies have shown that biphasic waveforms are generally superior to monophasic waveforms for achieving canine ventricular defibrillation. It further reports on additional tests directed at determining the significance of the duration of the initial phase. All of the tests for this study were conducted with a 10 millisecond truncated exponential waveform shock, and with the final current equal to 25% of the initial current. The timing of the polarity reversal was changed such that initial pulse durations of 1, 3, 5, 7 and 9 milliseconds were tested. The study concluded that ten millisecond biphasic truncated exponential waveforms are more effective with an initial pulse duration of 5 to 7 milliseconds, i.e., equal to or greater than the duration of the second phase.

U.S. Pat. No. 4,850,357—issued Jul. 25, 1989, and entitled: *BIPHASIC PULSE GENERATOR FOR AN IMPLANTABLE DEFIBRILLATOR;* is directed toward a circuit for delivering biphasic pulses without the need to short circuit the high voltage capacitor, which stores the energy for the pulses, at the end of a pulse. While not elaborating on the relative durations of the first and second phases of the pulse, the phases are shown to be equal, with the initial voltage of the second phase being equal to the terminal voltage of the first phase.

U.S. Pat. No. 4,821,723—issued Apr. 18, 1989, and entitled: *BIPHASIC WAVEFORMS FOR DEFIBRILLATION* is directed toward a method and apparatus for defibrillating a heart with a biphasic shock having an initial phase, the duration of which is at least slightly greater than the duration of the second phase. Further, the first phase of the biphasic waveform commences with a voltage magnitude equal to or greater than the initial voltage level of the second phase.

Referring to the paper: *Transthoracic Ventricular Defibrillation in the 100 Kg calf with Symmetrical One-Cycle Bidirectional Rectangular Wave Stimuli;* IEEE Trans Biomed. Eng. 30: 415, 1983, and to the paper: *Defibrillator of 100 Kg Calves with Asymmetrical, Bidirectional Rectangular Pulses;* Cardiovasa Res. 419, 1984, it is stated in U.S. Pat. No. 4,821,723 that: "Schuder and his associates were able to defibrillate 100 Kg calves using symmetrical biphasic rectangular waveforms at a lower range of energy and current, and to achieve a higher percentage of successful first shock defibrillations than with monophasic waveforms. Those same investigators obtained good results with asymmetrical biphasic waveforms in which the amplitude of the second phase of the shock was smaller than that of the first phase, and the two phases were of equal duration." This patent also sets forth the theory that the duration of the first phase of a biphasic waveform may have a significant effect on the extent of conditioning. It is further stated: "It appears that a short first phase, relative to the second phase, may be of insufficient duration to allow a conditioning process to be completed." As was previously set forth with respect to the Dixon paper, this study is based on the earlier postulation by Jones et al that the first phase conditions the heart cells to allow more effective defibrillation by the second phase.

Other efforts to reduce the size of an implantable defibrillator have been directed toward improvement of the electrodes through which pulses are applied to the heart for defibrillation purposes. U.S. Pat. No. 4,953,551—issued on Sep. 4, 1990 and entitled: *METHOD OF DEFIBRILLATING A HEART,* is primarily directed toward an improvement in the electrodes. However, the patent also advocates the use of an asymmetrical biphasic waveform. The asymmetrical waveform set forth is one in which the first and second phase, are of equal duration, but in which the initial voltage of the second phase is equal to the final voltage of the first phase, (voltage decays during the pulses on an exponential basis).

U.S. Pat. No. 4,998,531—issued on Mar. 12, 1991, and entitled: *IMPLANTABLE N-PHASIC DEFIBRILLATOR OUTPUT BRIDGE CIRCUIT* discloses a means for generating not only biphasic, but also monophasic, multi-phase or sequential defibrillation pulses. The patent is not particularly concerned with, nor does it discuss, the efficacy of biphasic pulses nor is it concerned with the relative durations of the first and second pulses.

U.S. Pat. No. 5,083,562 issued on Jan. 28, 1992, and entitled: *METHOD AND APPARATUS FOR APPLYING ASYMMETRIC BIPHASIC TRUNCATED EXPONENTIAL COUNTERSHOCKS,* sets forth a defibrillation therapy in which a first truncated exponential waveform of a first polarity has a first phase start amplitude and a first phase end amplitude and, a second truncated exponential waveform of second polarity opposite that of the first polarity, has a second phase start amplitude and a second phase end amplitude. The second phase start amplitude being lower than the first phase start amplitude and in a disclosed embodiment being substantially equal to the first end amplitude. Further, the second phase start amplitude is equal to substantially one half of the first phase start amplitude. This patent further teaches that the first and second phases are preferably of equal duration.

While there are many patents and papers in addition to those set forth above which relate to biphasic waveforms, the inventor is unaware of any which teach the advantage of the first phase being shorter than the second.

SUMMARY OF THE INVENTION

It is an object of this invention to provide a method and apparatus for improving the efficacy of defibrillators which provide biphasic truncated exponential waveforms. It is a further object of the method of this invention to provide biphasic defibrillation pulses to a heart wherein the relative durations of the phases have a predetermined relationship to each other, such that the energy, voltage, and current required for defibrillation is reduced from that required prior to the applicant's invention. It is a further object of this invention provide a defibrillator which generates biphasic defibrillation pulses in accordance with the applicant's invention wherein the energy, voltage, and current required for defibrillation is reduced from that which has previously been considered necessary.

In accordance with this invention, a method and apparatus of defibrillation is provided in which multiphasic pulses are applied to a heart with the first pulse being of a shorter duration than the second pulse. More particularly, in accordance with this invention, a defibrillator is provided wherein a biphasic, truncated exponential waveform is generated from a single capacitor discharge in which the first pulse is shorter in duration than the subsequent phase or phases. Further, a method of defibrillation is provided wherein a defibrillator provides a biphasic pulse, the duration ratio of the first pulse to the subsequent pulse in a preferred embodiment being approximately 40 to 60.

In its broader aspects; the method and apparatus of this invention is generally applicable to converting arrhythmias of the heart, particularly both atrial and ventricular tachycardia arrhythmias.

DETAILED DESCRIPTION OF THE PREFERRED EMBODIMENT

Figure 1:
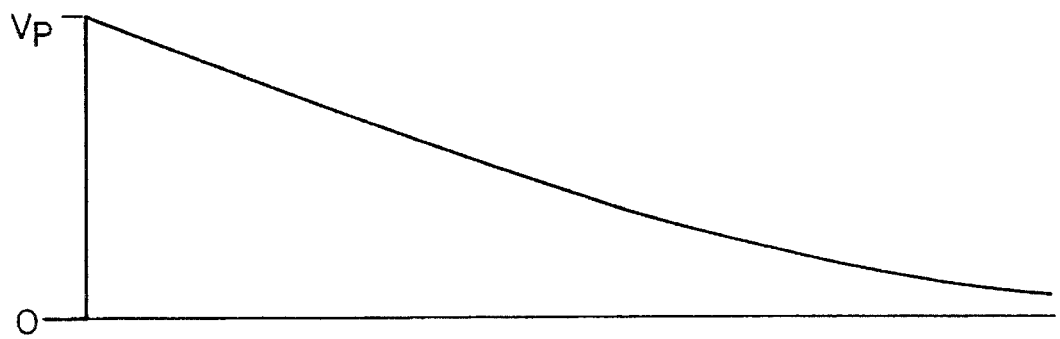
FIG. 1 shows the exponentially decaying waveform of a capacitor discharge into a resistive load.
Figure 2:
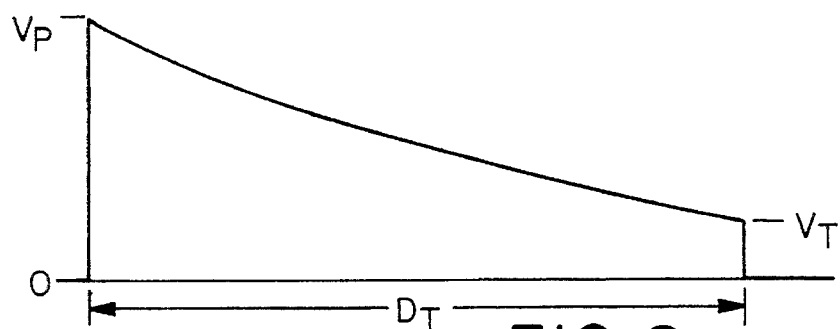
FIG. 2 shows a similar exponentially decaying waveform of the discharge of a capacitor into a resistive load, but which has been truncated.
Figure 3:
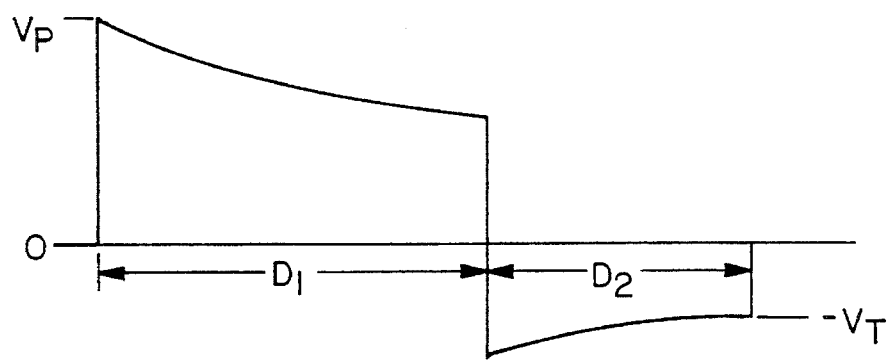
FIG. 3 shows the typical biphasic waveform of the output of a defibrillator in accordance with the teachings of the prior art as set forth above.

Generally, all current implantable defibrillation pulse generators and even some external generators use a capacitor discharge to deliver pulse energy to a heart to be defibrillated. The discharge of a charged capacitor into a resistive load, which is representative of a heart and attached defibrillation electrodes, results in a waveform with an exponential decay from a peak voltage $V_P$ as shown in FIG. 1. When a capacitor discharge is used for defibrillation, prior experimentation has established that stopping or truncating the discharge at a voltage $V_T$, before it reaches too low a level, as shown in FIG. 2, results in more efficacious defibrillation. Further, as set forth in the description of related art set forth above, it has been shown that causing a reversal of polarity during the discharge to produce a so-called biphasic waveform, as shown in FIG. 3, results in improved defibrillation efficacy as compared to a "monophasic" waveform such as shown in FIG. 2. Referring to FIG. 3, during the first phase, which has a duration $D_1$, the discharge voltage decays from $V_P$ to $V_S$. The polarity of the pulse applied to the heart is then reversed, with the voltage decaying during the second phase of a duration $D_2$ from $-V_S$ to $-V_T$. In accordance with the prior art, duration $D_1$ is typically equal to duration $D_2$, or longer, such as the 50/50% relationship shown in FIG. 3. A biphasic defibrillation waveform such as shown in FIG. 3 may be generated by any number of circuits, one of which is set forth in U.S. Pat. No. 4,850,357 issued Jul. 25, 1989 and assigned to the assignee of this application. The teachings of this patent while briefly set forth hereinafter, are incorporated herein by reference as an example of the type of circuit which might be used in practicing the teachings of this invention.

As set forth above in the description of related art, it has been the consensus of those skilled in the art that making the first phase of a biphasic waveform at least equal to or preferably longer in duration than the second phase provides the most effective defibrillation, all other parameters being the same. Further, biphasic waveforms have most frequently been used with the initial voltage of the second phase equal to the terminal voltage of the first phase, such that considerably less energy is conveyed through the electrodes to the heart by the second phase as compared to the first phase. This type of biphasic waveform facilitates the use of a single energy storage capacitor. However, if two capacitors are utilized, the initial amplitudes of each phase could be of equal magnitude or in any desired ratio of magnitudes.

Figure 4:
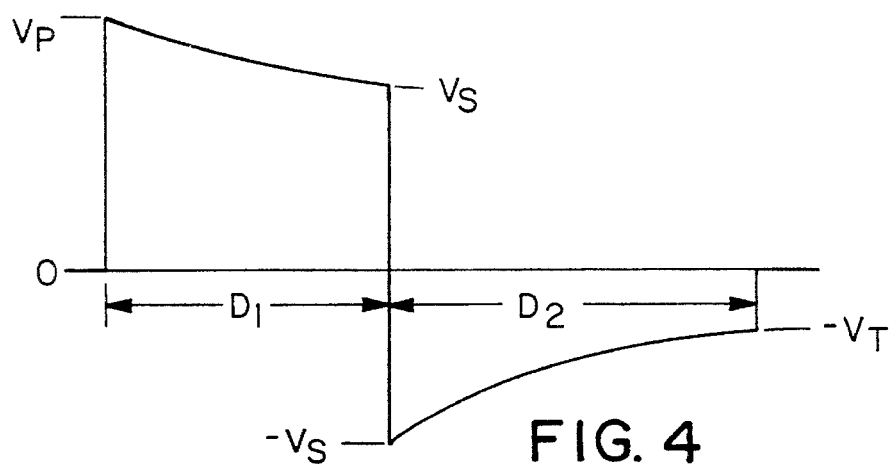
FIG. 4 shows the biphasic waveform generated by a defibrillator in accordance with this invention.

The applicant has now determined, contrary to the teachings of the prior art as set forth above, that the defibrillation efficacy of biphasic waveform pulses are improved by making the first phase shorter than the second. That is it has been determined, for instance, that the waveform shown in FIG. 4, wherein $D_1$ and $D_2$ are 40% and 60% respectively of the total pulse duration, has lower defibrillation strength requirements than the previously used biphasic waveform having equal first and second phases as is shown in FIG. 3, or longer first phases.

Having determined that the defibrillation strength requirements are lower with a shorter first phase, it is now possible: to reduce the size of the pulse generator, to increase the defibrillator safety margin, to provide a therapy which is more easily tolerated by the patient and to provide a higher implant success rate due to the more efficacious therapy, particularly when endocardial leads are used.

A biphasic pulse generator of the type shown in the above-mentioned U.S. Pat. No. 4,850,357 may, through circuit component adjustments, deliver pulses in accordance with the applicant's invention. However, the same has; not been previously done, wherein to do so was contrary to that which has been consistently taught in the prior art.

Figure 5:
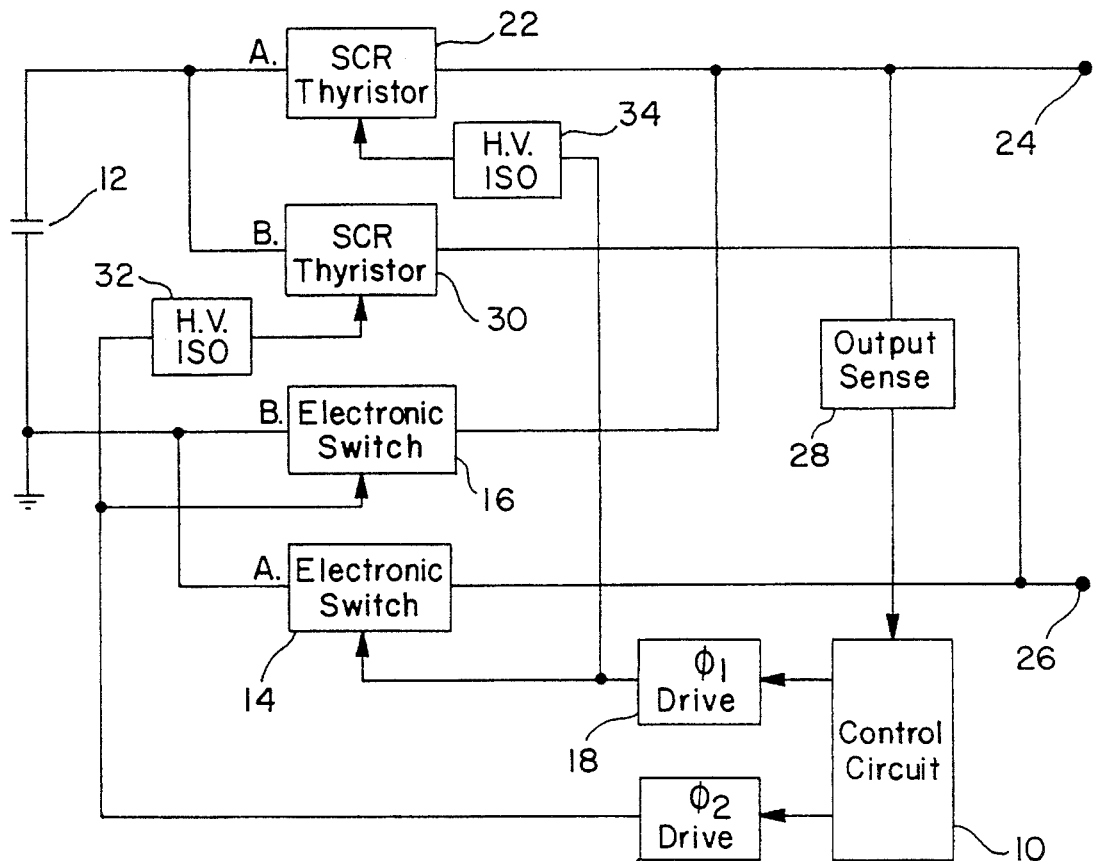
FIG. 5 is a block diagram of a pulse generator for an implantable defibrillator which is capable of delivering biphasic truncated exponential waveform in accordance with this invention.
Figure 6:
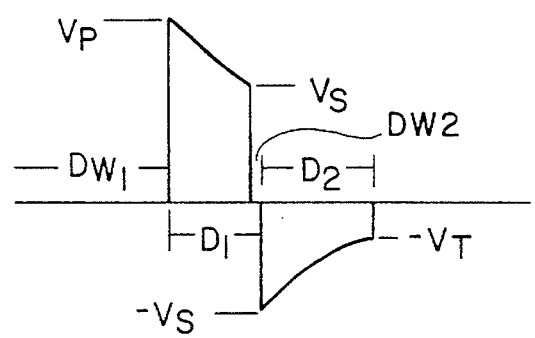
FIG. 6 is a biphasic defibrillator waveform in accordance with this invention such as could be delivered by the generator of FIG. 5.

Referring to FIG. 5, a block diagram of a biphasic pulse generator of the type set forth in the just mentioned patent is shown. FIG. 5 corresponds in general to FIG. 2 of the just mentioned patent. Control circuit 10 is a Four State Sequencer specifically designed to provide a first wait duration $D_{W1}$, a first pulse duration $D_1$, a second wait duration $D_{W2}$, and a second pulse duration $D_2$ by monitoring the voltage on capacitor 12 and providing timed signals to electronic switches 14 and 16 via drive circuits 18 and 20 respectively. An output waveform from the circuit of FIG. 5 in accordance with this invention is shown in FIG. 6. When drive circuit 18 is set high, the electronic switch 14 is allowed to conduct and a thyristor 22 is turned "on", such that the charge stored on capacitor 12 is delivered to the heart across electrodes 24 and 26 in a first polarity. After a first phase duration $D_1$ as determined by output sense circuit 28, drive circuit 18 is forced low turning off electronic switch 14 and thyristor 22. After a short delay $D_{W2}$, preferably less than 500 milliseconds, drive circuit 20 is set high turning on electronic switch 16 and a thyristor 30 thus, providing current of the opposite polarity to the heart. After second phase duration $D_2$ determined by output sense circuit 28, the electronic switch 16 is turned off which turns off thyristor 30. While the circuit of FIG. 5 is shown to provide wait durations $D_{W1}$ and $D_{W2}$ in FIG. 6, the duration $D_{W2}$ being significantly less than $D_1$ or $D_2$, it is not shown in the waveform of FIGS. 1–4.

In summary, the electronic switch 14 conducts to steer the low voltage side of the main storage capacitor 12 to electrode 26 while the high side is connected to electrode 24. Electronic switch 16 conducts to steer the low voltage side of the main storage capacitor 12 to electrode 24 while the high side is connected to electrode 26 The thyristor 22, when switch "on", provides the high voltage to electrode 24. The thyristor 30, when switched "on", provides the high voltage to electrode 26.

Output sense circuit 28 monitors the output across electrodes 24 and 26. When the output voltage across electrodes 24 and 26 falls to a predetermined level, the output sense circuit 28 will signal the control circuit 10, which then forces drive circuit 18 low. This shuts off electronic switch 14 and, therefore, thyristor 22. When the voltage applied across electrodes 24 and 26 falls to a still lower predetermined value, the output sense circuit 28 again signals the control circuit 10. This forces drive circuit 20 to be switched to a low, which shuts off electronic switch 16 and, therefore, the thyristor 30.

The high voltage isolation transformers 32 and 34 are used to isolate the thyristor drive circuits and prevent the transmission of undesired currents to them. Also, the high voltage isolation transformers are used to separate one section of the system from undesired influences of the other section.

The applicant has conducted studies with swine which establish the efficacy of a biphasic pulse having a shorter first phase in accordance with his invention. As hereinafter set forth, specific groups of different biphasic defibrillation waveforms were applied to each swine, with the data used to fit defibrillation probability of success curves for each waveform in each swine. The fifty percent probability of success was obtained for each waveform from the curves. Using appropriate statistical tests, the fifty percent probability of success levels were compared for significant differences. Six swine were tested in each study.

STUDY 1

Figure 7:
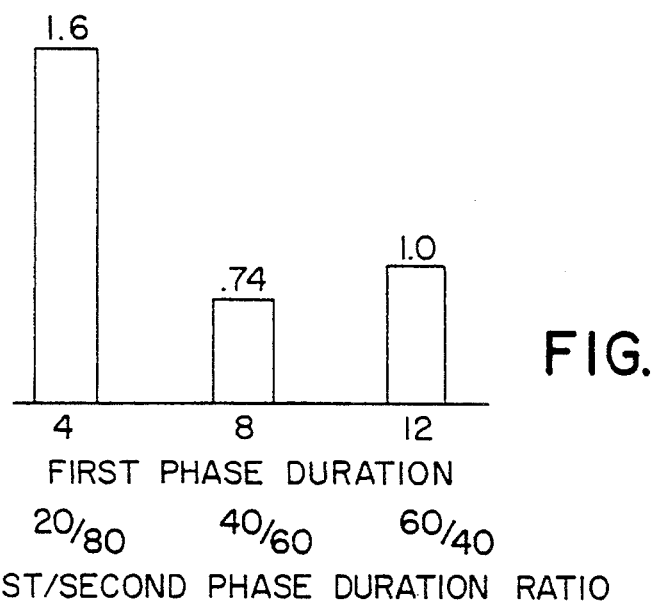
FIG. 7 is a chart setting forth the probability of a successful defibrillation while varying the relative durations of first and second phases of an 80% tilt biphasic waveform with the overall waveform length being held at a constant 20 milliseconds.

FIG. 7 is a bar chart showing the results of a study comparing the energy levels required for 50% probability of successful defibrillation for 20 millisecond, 80% tilt biphasic waveforms, wherein the duration of the first phase of the waveform was 4, 8 or 12 milliseconds. The length of each bar and the values above each bar represent a normalized value of the energy required for the 50% probability of successful defibrillation under otherwise like conditions. The 80% tilt referred to in FIG. 7 is determined by dividing the difference between the initial voltage and the final voltage by the initial voltage and expressing that value as a percentage. That is, if the initial voltage is 100 and the final voltage is 20, the tilt is 80%. Referring to FIGS. 1–4, and 6 showing defibrillator waveforms, $V_P$ is the initial (or peak) voltage and $V_T$ is the final (or trailing) voltage of the waveforms.

Prior to the applicant's invention, for a waveform with a total duration of 20 milliseconds, a minimum of 10 milliseconds duration for the first phase has been commonly used. This was based upon the teachings of the prior art that the first phase should be equal to or longer than the second. As set forth in FIG. 7, for a very short first phase duration, that is 4 milliseconds, the energy levels required for successful defibrillation were increased dramatically over that for a 12 millisecond first phase duration as used in the past. However, a significantly lower energy level resulted when comparing the previously used 12 millisecond first phase to an 8 millisecond first phase in accordance with this invention. This difference was statistically significant at the $p \leq 0.05$ level.

STUDY 2

Figure 8:
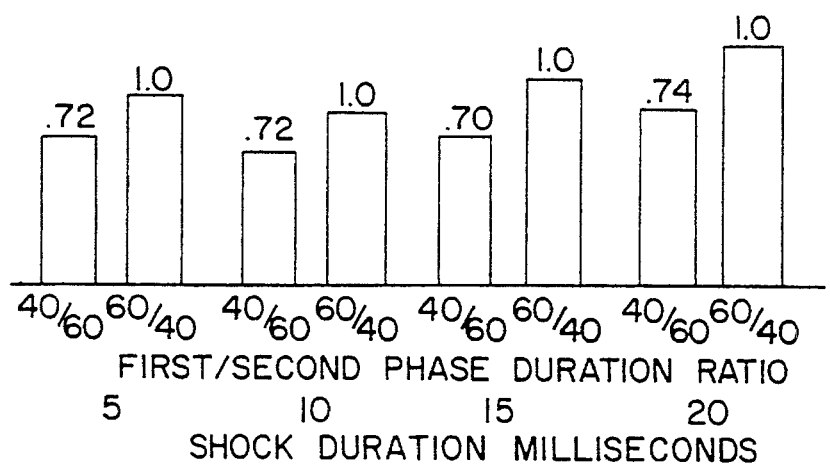
FIG. 8 is a chart comparing the energy required for successful defibrillation for 80% tilt waveforms of four different fixed durations with the duration of the first phase with respect to the second phase being 40/60% in accordance with this invention, and 60/40% a now generally accepted duration relationship.

FIG. 8 is a bar chart showing the results of a study conducted with 6 swine which considered biphasic waveforms of 5, 10, 15 and 20 milliseconds total durations and 80% tilt. The energy requirements for the 40–60% first phase to second phase durations of this invention were compared to those for 60–40% durations used in the past at each of the four total durations. The length of each of the bars and the values above each bar in FIG. 8 represents a per unit value of the energy required for fifty percent probability of successful defibrillation under otherwise like conditions. The pulse durations shown in milliseconds are the total durations for the biphasic waveforms. It should be noted that the energy requirements at all four total durations are lower for the 40–60 ratio in accordance with this invention compared to those for the 60–40% waveforms previously used. Energy requirements are reduced an average of 30 percent. Statistically significant differences were found at the 10, 15 and 20 millisecond total durations pulses.

STUDY 3

Figure 9:
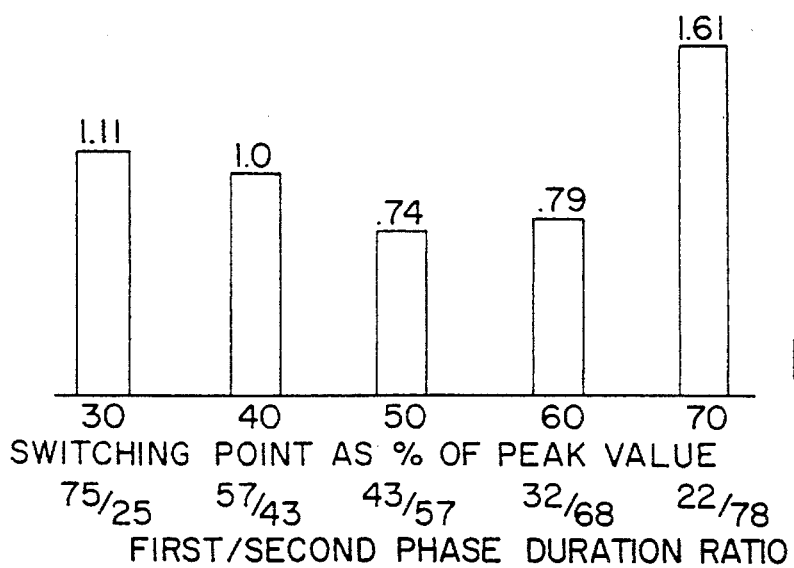
FIG. 9 is a chart comparing energy requirements with respect to the switching point from first to second phase as a percentage of peak voltage for a biphasic waveform.

FIG. 9 is a bar chart showing the results of a study conducted with 6 swine which considered biphasic waveforms having a fixed 10 millisecond total duration and an 80% tilt. The switch point between the first and second phase was varied and is expressed in the bar chart of FIG. 9 as occurring at a certain percentage of the initial voltage. The length of each bar and the value above each bar in FIG. 9 represents the value of the energy required for the same probability of successful defibrillation under otherwise like conditions normalized to the energy value at the 40% of peak voltage switching point. The switching point at 40% results in the previously used 60/40% biphasic waveform. Switching points greater than 40% decrease the relative duration of the first phase and increase the relative duration of the second phase. As shown in FIG. 9, increasing the switching point to 50% results in a 26% lower energy requirement than the previously used 40% switching point. The 50% of peak voltage switching point yields the preferred 40/60% biphasic waveform ratio in accordance with this invention.

In accordance with the teachings of the circuit shown in FIG. 5, the switching point in accordance with the previously used 60/40% ratio is at 40% of the initial voltage. In accordance with this invention, a preferred value of the switching point is at 50% of the initial voltage. Similarly, the termination voltage is determined by output sense circuit 28 as a percentage of the initial voltage which would remain unchanged at 20% of the initial value of V.

Biphasic truncated exponential pulses in accordance with this invention may also be provided by pulse generators wherein the relative durations of the first and second pulses are determined by a ratio-metric control circuit. That is, the first phase is still terminated at a voltage determined as a percentage of the initial voltage, but the duration of the first phase is measured and the second phase is terminated when its duration reaches a certain percentage of the duration of the first phase. Such a pulse generator is set forth in copending application Ser. No. 07/951,232, filed Sep. 25, 1992, entitled *METHOD AND APPARATUS FOR GENERATING MULTIPHASIC DEFIBRILLATION WAVEFORMS BASED ON PULSE WIDTH RATIOS*, which is assigned to the assignee of this application, and the teachings of which application are incorporated herein by reference.

Thus, in accordance with this invention, an improved method and apparatus for defibrillation of a heart is provided. The defibrillation method of this invention has improved performance characteristics, such that a defibrillator operated in accordance with this invention may be made smaller, compared to prior art defibrillations, the defibrillator safety margin may be increased and a higher implant success rate realized due to the more efficacious therapy provided by the invention.

It should be apparent to those skilled in the art that what has been described is considered at present to be the preferred embodiment of the defibrillation method and apparatus of this invention. In accordance with the Patent Statutes, changes may be made in the defibrillation method and apparatus without actually departing from the true spirit and scope of this invention. For instance, this invention is applicable to any biphasic or multiphasic waveform, with different shapes, i.e., square, ramp, triangle, sinusoidal, etc., of various tilts, and without regard to the particular circuit which develops the waveform. In the case of multiphasic waveforms, the first phase would be shorter than either the second phase or a combination of ensuing phases including the second. Further, this invention is not limited to defibrillation applications, but is generally applicable to converting arrhythmias of the heart, particularly both atrial and ventricular tachycardia arrhythmias. Finally, cardioverting shocks in accordance with this invention may be applied to the heart through either internal or external electrodes.

The appended claims are intended to cover all such changes and modifications which fall in the true spirit and scope of this invention.

We claim:

1. A method for defibrillating a heart by applying electrical energy shocks to the heart through electrodes, the method comprising:

A. applying a first shock having a first duration and a first polarity to the heart through the electrodes, B. applying at least a second shock, follwing said first shock, to the heart through the electrodes, said second shock having a second polarity opposite to said first polarity, and having a second duration which is longer than said first duration, a ratio of the duration of the first shock to the duration of the second shock being at least two to three but less than one to one.

2. The method of claim 1, wherein said first and second shocks form a biphasic truncated exponential waveshape.

3. The method of claim 2, wherein said first shock has an initial magnitude and said second shock begins with a magnitude of approximately 50 percent of the initial magnitude of the first shock.

4. The method of claim 3 wherein the duration of the second shock is approximately 1.5 times the duration of the first shock.

5. The method of claim 2, wherein said first shock has an initial magnitude and said second shock has a magnitude upon termination of approximately 20 percent of the initial magnitude of the first shock.

6. The method of claim 5, wherein a sum of the first duration of the first shock and the second duration of the second shock of the biphasic truncated exponential waveshape is between 2 and 20 milliseconds.

7. The method of claim 2, wherein the first duration of said first shock is 8 milliseconds and a sum of the first duration of the first shock and the second duration of the second shock of the biphasic truncated exponential waveshape is between 2 and 20 milliseconds.

8. A method for defibrillating a heart by applying electrical energy shocks to the heart through electrodes, the method comprising:

A. applying a first shock having a first duration and a first average magnitude to the heart through the electrodes, B. applying at least a second shock, following said first shock to the heart through the electrodes, said second shock having a second duration and a second average magnitude, said second duration being longer than said first duration and said second average magnitude being less than said first average magnitude, a magnitude ratio of the duration of the first shock to the duration of the second shock being at least two to three but less than one to one.

9. An electronic circuit for applying shocks through electrodes to a heart for converting an arrhythmia of the heart, said circuit comprising means for delivering a first shock having a first duration to the head through the electrodes, said circuit comprising means for delivering at least a second shock to the heart, following said first shock, to the head through the electrodes, said second shock having a second duration, said second duration being longer than said first duration, a ratio of the duration of the first shock to the duration of the second shock being at least two to three but less than one to one.

10. A system for converting an arrhythmia of a heart by applying electrical energy shocks to the heart, said system comprising:

A. a sensing means for sensing an arrhythmia of the heart,

B. a first shock delivery means responsive to the sensing means for delivering a first shock of a first duration and a first average magnitude to the heart, C. a second shock delivery means responsive to the sensing means and the first shock delivery means for delivering a second shock of a second duration and a second average magnitude to the heart, said second duration being longer than said first duration, a ratio of the duration of the first shock to the duration of the second shock being at least two to three but less than one to one.

11. The system of claim 10, wherein said second average magnitude is less than said first average magnitude.

12. The system of claim 10, wherein said first and second shocks form a biphasic truncated exponential waveshape.

13. The system of claim 12, wherein said first shock terminates and said second shock begins witch a magnitude of approximately 50 percent of the initial value of the first shock.

14. The system of claim 12, wherein said second shock terminates with a magnitude of approximately 20 percent of the initial value of the first shock.

15. The system of claim 14, wherein a sum of the first duration of the first shock and the second duration of the second shock of the biphasic truncated exponential waveshape is between 2 and 20 milliseconds.

16. The system of claim 12, wherein the first duration of said first shock is 8 milliseconds and a sum of the first duration of the first shock and the second duration of the second shock of the biphasic truncated exponential waveshape is between 2 and 20 milliseconds.

* * * * *